United States Patent [19]
Poku et al.

[11] Patent Number: 5,756,885
[45] Date of Patent: May 26, 1998

[54] METHOD FOR DETERMINING THE CLEANLINESS OF A SURFACE

[75] Inventors: Isaac T. Poku, Austin; Rama Cherkur, Cedar Park, both of Tex.

[73] Assignee: Motorola, Inc., Schaumburg, Ill.

[21] Appl. No.: 628,048

[22] Filed: Apr. 4, 1996

[51] Int. Cl.$^6$ .................................................. G01N 13/02
[52] U.S. Cl. ................................................................ 73/104
[58] Field of Search ........................... 73/104; 356/372, 356/379, 384, 388, 394, 397; 348/87, 92, 128

[56] References Cited

U.S. PATENT DOCUMENTS

| | | | |
|---|---|---|---|
| 3,618,374 | 11/1971 | Miller . | |
| 3,733,893 | 5/1973 | Bickford et al. | 73/104 |
| 4,824,230 | 4/1989 | Litt | 356/397 |
| 5,150,608 | 9/1992 | Mazzoleni et al. | 73/81 |
| 5,275,667 | 1/1994 | Ganesan et al. . | |

OTHER PUBLICATIONS

G.S. Ganesan, et al.; "Contact Angles as a Measure of Interfacial Integrity: Theory and Experiments;" EEP. vol. 10-2, Advances in Electronic Packaging; pp. 717–722; ASME (1995).

*Primary Examiner*—Robert Raevis
*Attorney, Agent, or Firm*—Patricia S. Goddard; Jeffrey S. Abel

[57] ABSTRACT

A method for determining the cleanliness of a surface of a substrate involves using a visual pattern (17, 29). The visual pattern is either provided in the optical portion of a visual system or is formed on the surface of the substrate to be analyzed. A liquid droplet (26, 27) is dispensed onto the substrate surface, and the extent of the spread area of the droplet is compared to the visual pattern. If the area of the droplet is greater than or equal to a tolerance as signified by the pattern markings, then the surface of the substrate is determined to be sufficiently clean. In relying upon a simple visual comparison of the area of the surface covered by the droplet with an empirically determined visual pattern, a method for analyzing surface cleanliness is consistent between operators and surfaces, is easy to set up and operate, and improves manufacturing throughput.

5 Claims, 3 Drawing Sheets

5,756,885

1

METHOD FOR DETERMINING THE CLEANLINESS OF A SURFACE

FIELD OF THE INVENTION

The present invention relates to methods for determining the cleanliness of a surface in general, and more particularly to determining that the cleanliness of a surface of an element used in a packaged semiconductor device is within a tolerance before encapsulating an integrated circuit die.

BACKGROUND OF THE INVENTION

In the integrated circuit industry, integrated circuits are mounted on lead frames or wiring substrates and are encapsulated in a material to form a final packaged integrated circuit. First, integrated circuits are formed in mass on one or more integrated circuit wafers. The integrated circuits are then segmented from the integrated circuit wafers to form individual singulated integrated circuits, also known as chips or semiconductor die. The lead frame or wiring substrate is then provided wherein an adhesive material is placed in contact with the lead frame or wiring substrate. The integrated circuit die is then brought in contact with the adhesive material on the lead frame to attach the integrated circuit to the lead frame. Electrical connections are then made between the die and the lead frame or wiring substrate, for example by wire bonding, tape automated bonding, or flip-chip bonding, so that the integrated circuit die can perform electrical communication with the external world. The integrated circuit and portions of the lead frame or wiring substrate are then encapsulated in a plastic material to protect the sensitive integrated circuitry from environmental influences.

This packaging operation results in a final device that has many interfaces between many materials. If the surface of the integrated circuit is not sufficiently clean, then the integrated circuit will not properly adhere to one or more of the plastic encapsulation material or to the lead frame or wiring substrate. Critical surfaces which usually results in significant yield loss if not properly cleaned are those surfaces which form an interface with the plastic molding compound, including surfaces of the integrated circuit die, the lead frame or wiring substrate, and the die attach material. If not properly cleaned, these interfaces are weak and will delaminate or crack due to internal stresses which are imposed during high temperature attachment of the package to a user's board. Therefore, it becomes absolutely critical for an integrated circuit manufacturer to not only clean these various surfaces, but to accurately determine whether these surfaces are sufficiently clean to within specific manufacturing tolerances.

One method to measure the cleanliness of a surface of an integrated circuit or other element used in semiconductor manufacturing is to use an apparatus known as a goniometer. To use the goniometer, a drop of liquid, such as water, is placed onto the surface which is to be measured for cleanliness. For example, FIG. 1 illustrates a substrate 10 having a top surface 11, wherein the cleanliness of surface 11 is to be determined. In FIG. 1, a volume of liquid is placed onto the surface 11 to form a droplet 12. The droplet 12 will spread across the top surface 11 to form a contact angle theta (θ) between the droplet edge and the surface 11. (The contact angle can also be defined as the supplementary angle to θ.) The goniometer is an optical device which when aligned properly to the substrate and the droplet in a cross-sectional manner (in other words, when viewed from the side), allows for the contact angle of droplet 12 to be accurately measured. FIG. 1 illustrates a small contact angle θ. The cleaner the surface 11 is, the smaller the contact angle (or the larger the supplementary contact angle). For purposes of semicon-

2 ductor assembly operations, contact angles of less than 10° are considered to be acceptable levels of cleanliness for sufficiently strong package interfaces.

FIG. 2 illustrates a surface 11 which is not sufficiently clean for integrated circuit packaging. In FIG. 2, a droplet 14 placed on the surface 11 of the substrate 10 has a contact angle θ' that is significantly greater than 10°. Because contact angle θ' is greater than a specified tolerance for semiconductor assembly, it can be said that the substrate 10 has a surface 11 which is not sufficiently clean for high yield integrated circuit processing.

As previously mentioned, the contact angle is measured using the goniometer device. The goniometer must be placed and aligned parallel with the surface of the substrate so that the contact angle can be measured by viewing the droplet from the side. In a manner similar to a protractor, an edge of the goniometer is aligned to a specific point on the water droplet to obtain the proper contact angle measurement. When this positioning and set-up of the goniometer is achieved, the contact angle can be measured via various angle markings located on the optical portion of the goniometer.

There are several problems with the goniometer method for determining the extent of surface cleanliness. First, the measurement of the contact angle tends to be very subjective and varies from operator to operator. Therefore, the measurements are not very repeatable, varying from person to person and from wafer to wafer in a manner that is not acceptable for a quality manufacturing environment. In addition, the goniometer is not an easy device to set up and operate. The level of training required to operate and properly measure contact angles using a goniometer is excessive. Furthermore, the person operating the goniometer must work quickly to ensure that the contact angle is measured within a short time if being dispensed, else the droplet will begin to change shape and angle due to vibrations, ambient turbulence, or other environmental forces acting on the droplet. However, due to the complexity of goniometer measurements by operators, working as fast as needed to prevent changes in droplet shape and angle is not always achieved. The time it takes to measure contact angles not only affects accuracy of the results, but also adversely affects throughput of assembly operations due to the large amount of set-up time and alignment time that is needed.

For at least these reasons, the goniometer technique is not very feasible when used in a mass manufacturing environment. Therefore, a need exists in the semiconductor industry for a method for finding surface cleanliness of integrated circuits and other elements used in semiconductor manufacturing which has increased throughput, is less subjective, and can be easily implemented and set-up by operators in a mass manufacturing environment.

DETAILED DESCRIPTION OF A PREFERRED EMBODIMENT

Generally, the present invention provides a method for determining the cleanliness of a surface of a substrate wherein a droplet of fluid is dispensed on the surface of the substrate, and the area of the droplet is compared to the area of a visual pattern which signifies a level of cleanliness. The visual pattern can be in the form of graduations such as rings, hash marks, tick marks, or dots which are placed at predetermined locations. The visual marks may be provided either on the substrate which is being analyzed, or in an optical system, such as in an optical eye piece or on a video display screen. Because the amount of fluid dispensed is a known and controlled volume, the markings of the visual pattern can be set to correspond to an acceptable area or radius for this known volume of fluid, for the particular type of fluid being used, and for the type of surface being analyzed.

By comparing the approximately circular area of the droplet of fluid with an area bounded by the markings in the visual pattern, an operator can easily determine whether the substrate is sufficiently clean on a pass or fail ("go" or "no go") basis. There is no need for an operator to determine the actual contact angle of the droplet of fluid, and therefore the subjectivity and inaccuracies of contact angle measurement as previously discussed are eliminated by practicing the present invention. Not only does the present invention simplify an operator's job, but increase throughput because the visual comparison is faster than measuring a contact angle with a goniometer. Furthermore, measuring the cleanliness of a substrate in accordance with the invention can be automated to further increase throughput. An image recognition system, such as pattern recognition, intensity of reflected light monitoring, optical scanning, and the like, used in conjunction with a computing system can be used to compare the area of the fluid droplet with the appropriate markings of the visual pattern. By fully automating the system using an electronic visual recognition or computer system, all human subjectivity and judgment can be eliminated, thereby increasing the accuracy, reliability, and speed of the cleanliness determinations.

These and other features and advantages of the present invention will be more clearly understood from the following detailed description taken in conjunction with the accompanying drawings. It is important to point out that the illustrations may not necessarily be drawn to scale and that there may be other embodiments of the present invention which are not specifically illustrated.

Figure 3:
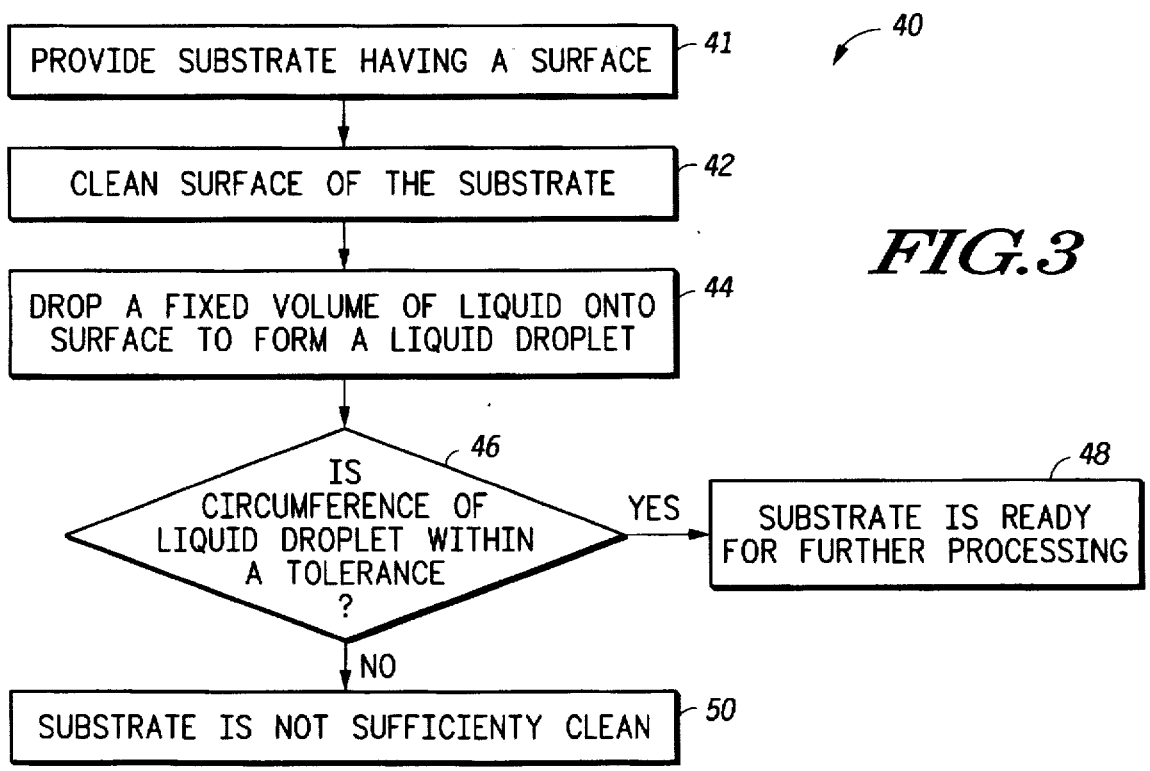
FIG. 3 illustrates, in a flow chart, a method for measuring surface cleanliness of a substrate by observing in a top-down manner a radius, circumference, or area of a liquid droplet placed on the surface in accordance with the present invention.

FIG. 3 illustrates a process flow 40 which includes steps 41, 42, 44, 46, 48, and 50, in accordance with one embodiment of the present invention. A first step in process flow 40 is a step 41, which is the step of providing a substrate having a surface, wherein the cleanliness of the surface needs to be evaluated. The type of substrate surface, the cleanliness of which is being evaluated, is unlimited with the present invention. However, in one application the substrate is an element used in semiconductor device assembly. For example, the substrate can be: a metal lead frame; a flexible circuit; an organic wiring board, such as a printed circuit board; a ceramic substrate; a semiconductor wafer, wherein the surface analyzed for cleanliness is either the active side of the wafer or the back side; or an individual semiconductor die which has been singulated from a semiconductor wafer, again wherein the surface is either the active side or the back side of the die.

In semiconductor assembly operations, the cleanliness of the various foregoing elements is important to ensure proper adhesion between different materials in a final packaged semiconductor device. For example, it is important to have good adhesion between the semiconductor die and the lead frame so that upon encapsulating the die and lead frame in plastic, the die-lead frame interface can withstand internal stresses. An example of internal stresses which this interface is likely to see are those imposed by temperatures associated with the board mounting or surface mounting process performed by a user to attach the device to a board. The stresses imposed can result in delamination at weak interfaces, such as the die-to-plastic interface, the die-to-lead frame interface, and between the lead frame-to-plastic interface. Such delamination compromises the integrity of the final packaged device. Delaminations can be avoided or at least minimized by ensuring adequate cleanliness of the surfaces at the various interfaces, hence the usefulness of the present invention.

Upon establishing the surface which is to analyzed, be it that of a semiconductor element or otherwise, a next step of process flow 40, step 42, is a step of cleaning the surface of the substrate. In a semiconductor package assembly process, surfaces of the elements discussed above will typically be cleaned. Cleaning is typically done because the various elements have been subjected to various handling operations, processes, and storage conditions which could cause contamination on the surfaces. The present invention can be used to determine whether the cleaning operations have been effectively accomplished, or whether any cleaning or additional cleaning is necessary. In the context of semiconductor package assembly, the various elements such as the die, lead frame, or printed circuit board, can be cleaned with a variety of chemical, or physical processes, or combinations thereof. For example, one common method for cleaning these elements is ultraviolet (UV) radiation. UV radiation, both with and without the presence of ozone, has proven to be a successful means for cleaning organics and other contaminants from surfaces to establish improved material interfaces in the final packaged semiconductor device without damaging the elements.

While process flow 40 includes a cleaning step 42, such a step is an optional part of practicing the invention. The remaining steps of the process flow can be used in accordance with the invention to analyze the cleanliness of the substrate surface without having performed a cleaning operation. For example, one may determine that the level of cleanliness of a substrate surface is sufficient by using methods taught herein, and therefore there is no need to clean the surface of the substrate. Thus, the present invention can be used to eliminate unnecessary cleaning operations which might otherwise be performed as a precautionary measure to improve throughput and reduce waste.

A next step in flow 40 is a step 44 which involves dropping a known volume of liquid onto the surface of the substrate. A very small amount of fluid is sufficient, for example a microliter ($\mu$L), as can be dispensed using a micropipette or microsyringe. Upon dispensing, the fluid will spread and form a liquid droplet. Preferably the surface is substantially planar so that the droplet formed can take a shape which is not dictated by, or dependent upon, the underlying topography of the substrate.

As discussed previously, the extent of the spread over the surface of the substrate can be used as a measure of the cleanliness of that surface. While in prior art techniques, the contact angle that the liquid droplet made with the surface was used to determine the cleanliness of that surface, in the present invention, the area or extent of the spread of the liquid droplet is used to determine the cleanliness of that surface. Barring any irregularities on the surface of the substrate, the liquid droplet will take an approximately circular shape when viewed from the top due to natural surface tension forces. For a known volume of fluid, the circular area of the droplet will vary depending on the cleanliness of the surface. As compared to the contact angle of the droplet, the circular area will increase as the contact angle decreases. In accordance with the present invention, the area or extent of the spread of the liquid droplet is compared to a known acceptable area which is empirically determined. The known acceptable area is included in a visual pattern with which the liquid droplet can be compared. In a preferred form, the visual pattern and the liquid droplet are overlaid with one another to maximize the accuracy of this comparison.

Figure 4:
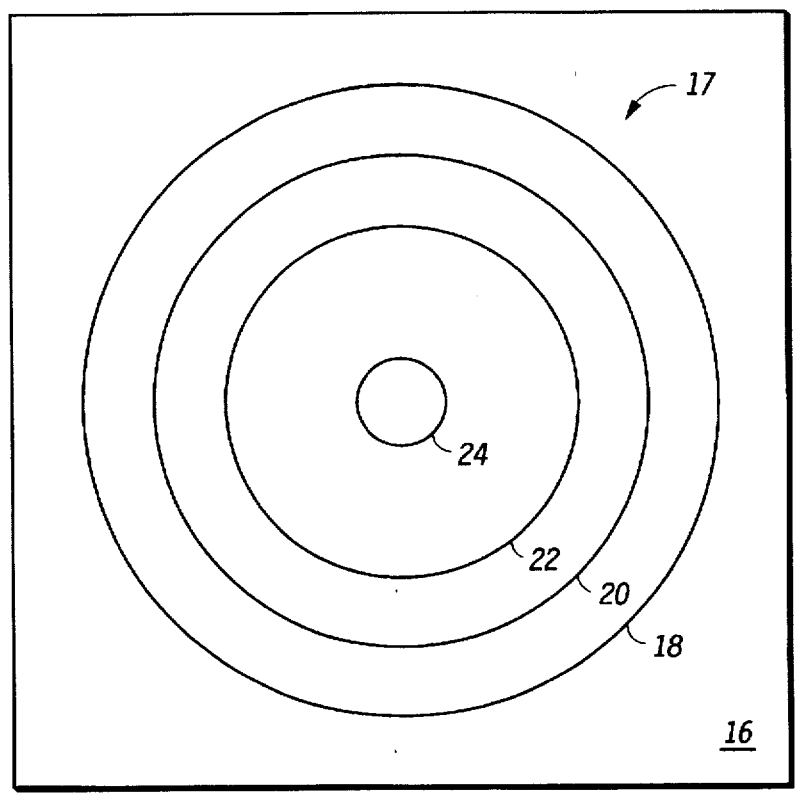
FIG. 4 illustrates, in a top view, a visual pattern having concentric rings wherein areas enclosed by the rings are compared to the area of a liquid droplet in accordance with the present invention.

FIG. 4 illustrates one example of a visual pattern 17 which is suitable for practicing the present invention. Visual pattern 17 includes a field of view 16 of optical system and a plurality of rings 18, 20, 22, and 24 within the field of view. Rings 18–24 define their own enclosed areas which will be measured against the spreading area of a liquid droplet formed on the substrate surface. In one embodiment, each of the rings can be used to measure a different level of cleanliness on the same substrate surface, using the same volume of dispensed fluid, and the same type of dispensed fluid. In another embodiment, each of the rings may signify an acceptable area for different types of fluids which may be dispensed. For example, water or alcohol may be the fluid that is dispensed on the substrate to determine cleanliness. In a first form, ring 22 may represent an acceptable level for dispensing a known volume of water. In another form, alcohol may be used to determine the cleanliness of the surface, and ring 20 may define the acceptable level of cleanliness for a surface when using a fixed volume of alcohol dispensed on the surface.

Visual pattern 17 can be viewed in any one of several ways. For example, visual pattern 17 can be incorporated into the substrate whose surface is being measured. For example, in a semiconductor wafer, rings 18–24 can be formed as metal rings or lines beneath a planar dielectric layer of the wafer. The rings are visible through the dielectric layer, and therefore can be used as a visual pattern in accordance with the present invention. Alternatively, visual pattern 17 can be incorporated into an optical system used to view the droplet of fluid which has been dispensed on the surface. In one form, the optical system can be an optical eye piece, wherein rings 18–24 are included in the viewing path of the operator. In another embodiment, the optical system may be an electronic imaging system which generates visual pattern 17 onto a display screen or monitor.

Figure 1:
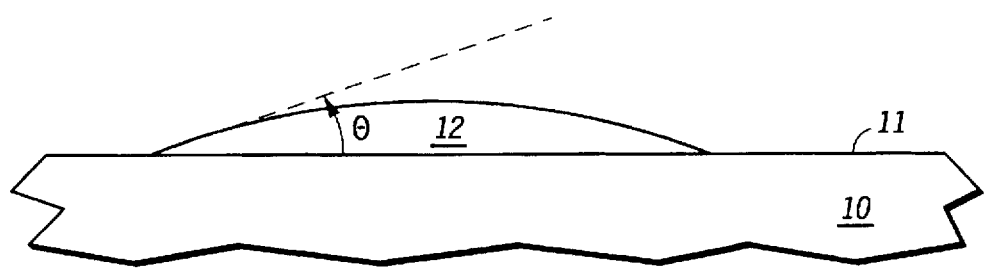
FIG. 1 illustrates, in a cross-sectional view, a prior art technique for providing a drop of liquid on a clean surface to form a contact angle theta (θ) which is measured by a goniometer to determine that the surface is within a cleanliness tolerance.
Figure 2:
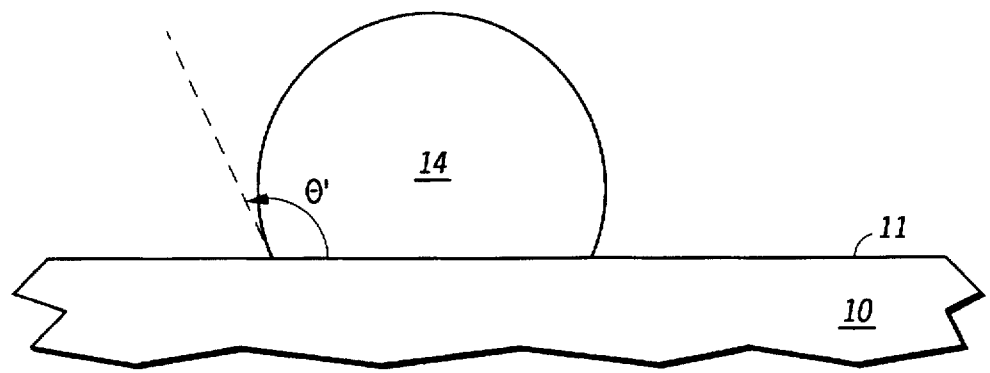
FIG. 2 illustrates, in a cross-sectional view, the goniometer technique of FIG. 1 wherein the surface is not clean and has a large contact angle θ'.

Upon providing visual pattern 17 in any of the forms previously described, or an equivalent form, the substrate surface having the liquid droplet dispensed thereon is compared against the visual pattern 17. Specifically, the droplet is viewed preferably from a direction perpendicular to the substrate surface, as compared to viewing the droplet from the side in prior art contact angle measurement techniques. For example, in reference to FIG. 5, a liquid droplet 26 is dispensed on a substrate surface and is brought into the field of view 16. The substrate surface lies in the plane of the figure so that the direction of view or line of sight is perpendicular to the figure and the surface. Upon dispensing, the liquid disperses to form a droplet. As illustrated, the circumferential area of liquid droplet 26 falls between the circumferential areas of rings 20 and 22 in visual pattern 17. An operator can easily compare the areas of the droplet 26 with rings 18–24 to determine whether the cleanliness of the surface is adequate. All that the operator needs to know is which ring corresponds to the acceptable level of cleanliness for the type and amount of fluid dispensed, and the type of surface being analyzed. In one embodiment, each of rings 18–24 may represent different degress of cleanliness, in which case the surface being analyzed in FIG. 1 has a cleanliness of that signified by ring 22. Alternatively, the various rings may represent a single acceptable level of cleanliness, but for different types or volumes of liquid dispensed. In another form, the rings could represent acceptable levels of cleanliness for different surfaces being analyzed (e.g. a die active surface, a die back side, a lead frame, etc.).

For purposes of illustration only, assume that ring 22 of visual pattern 17 corresponds to an acceptable level of cleanliness for a known volume of water as dispensed on a back side or inactive surface of a semiconductor die. According to FIG. 5, the cleanliness of the back side of the die is acceptable, because the area of liquid droplet 26 extends beyond the area of ring 22. Recall that the cleaner the surface, the larger the area of spread of the liquid droplet. If on the other hand, the same amount of water is dispensed on the back side of the semiconductor die where the cleanliness of the back side of the die is unacceptable, the liquid droplet will fall inside the boundary of ring 22. This case is illustrated in FIG. 6 where a liquid droplet 27 has an area which is smaller than the circumferential area of ring 22. If ring 22 is the gauge for an acceptable level of cleanliness, the surface being measured in FIG. 6 has an unacceptable cleanliness.

Figure 5:
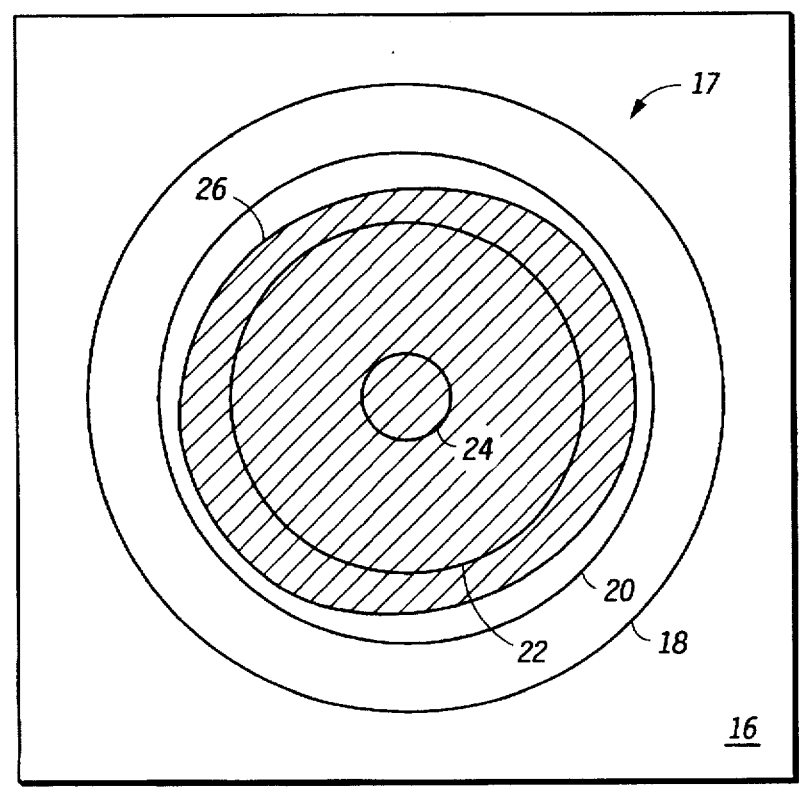
FIG. 5 illustrates, in a top view, the measurement of a liquid droplet on a clean surface in accordance with the present invention.
Figure 6:
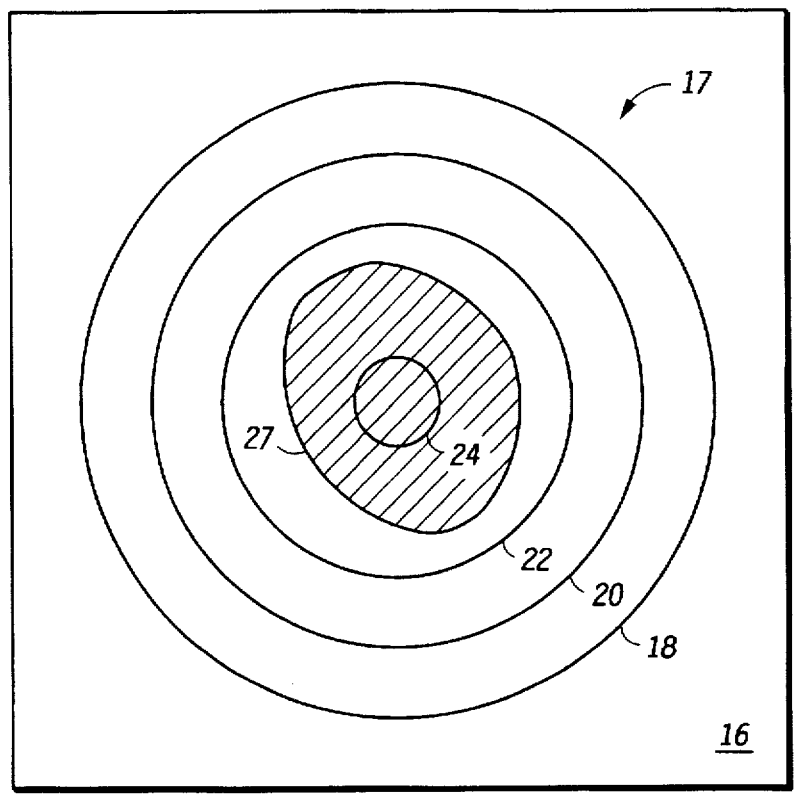
FIG. 6 illustrates, in a top perspective view, the measurement of a liquid droplet on a surface which is not sufficiently clean in accordance with the present invention.

In reference to process flow 40, the comparison of the area of the liquid droplets to the visual pattern just discussed in reference to FIG. 5 and FIG. 6 is included in the process flow as a step 46. Step 46 is used to determine whether the circumference of the liquid droplet falls within a tolerance range, wherein the tolerance range is incorporated into visual pattern. In reference to FIGS. 5 and 6, the tolerance was the area enclosed by ring 22. If the liquid droplet has an acceptable level of cleanliness (i.e. is within the tolerance) the substrate moves on to further processing as indicated by a step 48 of process flow 40. For example, in the context of a semiconductor package assembly process, if the die back side and a lead frame surface are determined to be sufficiently clean, a next step in the assembly operation of attaching the die to the lead frame can be performed. If, however, it is determined that the surface is not sufficiently clean (i.e. is outside of the tolerance), as in a step 50 of process flow 40, appropriate remedial actions may be taken. For example, the substrate may undergo an additional cleaning operation. Alternatively, the substrate could simply be scrapped as not suitable for further processing.

Figure 7:
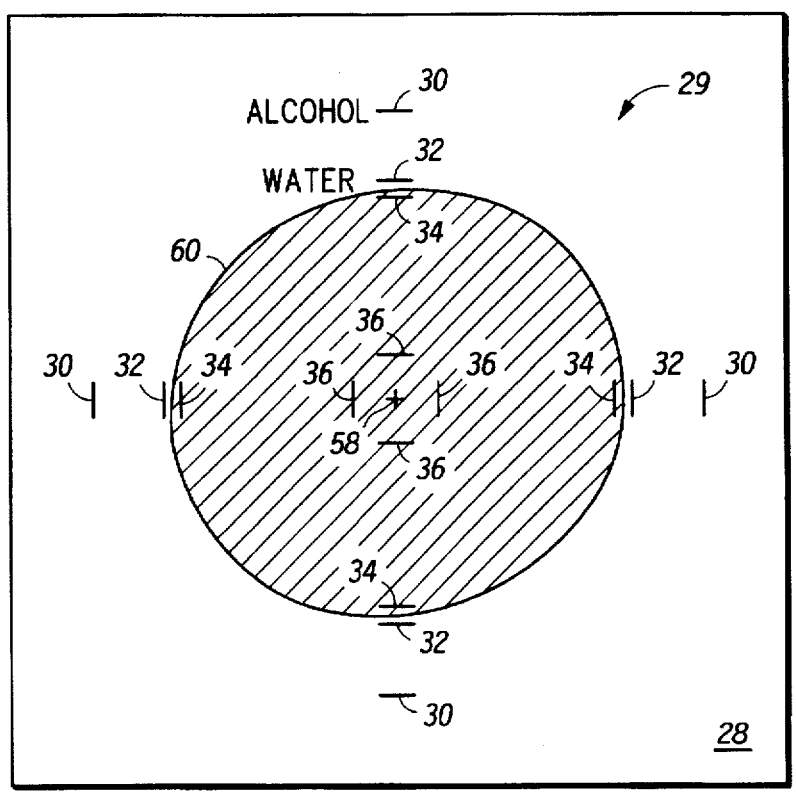
FIG. 7 illustrates, in a top view, an alternate visual pattern which can be used to determine surface cleanliness in accordance with another embodiment the present invention.

It is important to note that the concentric rings of visual pattern 17 are not necessarily the only type of visual pattern which can be used to practice the present invention. A variety of markings can be incorporated into an optical system or onto a substrate whose cleanliness is being measured to fulfill a goal of identifying or signifying an acceptable level of cleanliness. An example of an alternative marking is illustrated in FIG. 7, wherein a field of view 28 includes a visual pattern 29 made up of a plurality of hash marks (or tick marks) in the overall form of a cross. Hash marks 30, 32, 34, and 36, like concentric rings 18–24, can represent either varying levels of cleanliness when using a same type and same amount of dispensed fluid, acceptable levels for differing types of fluids, acceptable levels for different amounts of fluids, or acceptable levels for difference surface types being measured.

Upon dispensing a liquid droplet 60, its area can be compared to the location of the hash marks. The liquid droplet is approximately centered around a center 58 of the viewing pattern and the outer boundary of the liquid droplet 60 is determined to fall within certain boundaries or beyond certain boundaries as defined by the hash marks. For example, as illustrated in FIG. 7, liquid droplet 60 falls beyond the boundaries set by hash marks 34, but within the boundaries set by hash marks 32. An operator can simply view where the liquid droplet falls relative to the hash marks, and determine whether or not this particular location is acceptable for the type of fluid, the amount of fluid, and the type of surface being measured.

To further aid the operator, the visual pattern may include text identifying acceptable levels. For example, as illustrated in FIG. 7, hash marks 32 include characters indicating that this is the acceptance level for dispensing water, while hash marks 30 signify an acceptance level for dispensing alcohol on the surface. (Although it is noted that one need not use water or alcohol to practice the invention.) As is shown, droplet 60 does not extend to either of hash mark 30 or 32, and therefore would not represent an acceptable level of cleanliness if droplet 60 is either one of water or alcohol.

The foregoing detailed description and illustrations contained herein demonstrate many of the advantages associated with the present invention. In particular, it has been revealed that the cleanliness of a surface of a substrate can be easily measured without having to precisely determine the contact angle which a droplet of fluid makes with the surface. Instead, the circumferential area or spreading area of a known volume of fluid can be compared against a predetermined visual pattern which signifies acceptability of the surface cleanliness. For a given volume of fluid, a given type of fluid, and a given type of surface whose cleanliness is being analyzed, an acceptable level of cleanliness can become a permanent mark in the visual pattern. The area of the mark, whether it be in rings, hash marks, or some other visual feature, when compared to the area of the liquid droplet can be used to easily gauge whether the surface of the substrate is sufficiently clean. An easy visual comparison of the droplet with a visual pattern enables an operator to give a quick pass or fail assessment of the cleanliness of the surface. The need for an operator to impose judgment or subjectivity to the contact angle is eliminated by practicing the invention, and cleanliness determinations can be performed much faster by an operator than by using a traditional goniometer to measure contact angle. Furthermore, because only a visual comparison is made to determine the cleanliness of the surface, a method in accordance with the present invention can be automated in conjunction with a image recognition system, thereby further enhancing the speed at which cleanliness of a substrate can be determined.

Thus, it is apparent that there has been provided in accordance with the invention, a method for determining or analyzing the cleanliness of a surface that fully meets the needs and advantages set forth previously. Although the invention has been described and illustrated with reference to specific embodiments thereof, it is not intended that the invention be limited to these illustrative embodiments. Those skilled in the art will recognize that modifications and variations can be made without departing from the spirit of the invention. For example, while semiconductor package assembly is one particular area in which the present invention has beneficial applicability, it is important to realize that the invention is likely to provide similar benefits for any operation wherein the cleanliness of a surface is an important parameter for successful processing. Furthermore, it is important to note that the present invention is not limited to dispensing any particular type or amount of fluid. Water, alcohol, other solvents, or even molten metals, such as solder may be used as the fluid taught herein.

Other aspects of the invention which is not restricted by the specific embodiments described are the visual patterns and optical systems used to perform the inventive method. The patterns and systems herein described and illustrated are merely representative of suitable visual patterns which may be used. It is envisioned, that other visual patterns may be acceptable, and may be optimized for various features which may exist on the surface whose cleanliness is being measured. For example, the visual pattern can be color coded for optimal contrast with the surface being measured. Further, the color coding can be used to signify differing cleanliness or acceptance levels. In addition, it is recognized that the visual pattern may be incorporated in many forms. For instance, the visual pattern may be shown as a template or overlay on a video monitor, and the liquid droplet is placed under a microscope whose image is transmitted to the video display monitor, with the template overlaid. Furthermore, the visual pattern may be incorporated either internally or externally with an eye piece such as a magnification lens. Alternatively, the visual pattern may itself be formed in the substrate, but visible from the surface whose cleanliness is being measured. Each of these visual patterns, and equivalents thereof, are within the scope of the present invention. Moreover, a single visual system can be designed to incorporate a visual pattern which signifies acceptable cleanliness levels for different fluids, different surface types, or different fluid amounts. Alternatively, multiple visual systems could be designed, one each for a particular type and amount of fluid and a particular surface type. Therefore, it is intended that this invention encompass all such variations and modifications as fall within the scope of the appended claims.

We claim:

1. A method for measuring cleanliness of a surface comprising the steps of:

providing a substrate having the surface, the substrate having a visual pattern formed therein;

dispensing a known volume of fluid on the surface of the substrate, on the visual pattern;

comparing an area of the known volume of fluid dispensed on the surface with the area of the visual pattern to determine if the surface is sufficiently clean.

2. The method of claim 1 further comprising the step of cleaning the surface of the substrate prior to dispensing the known volume of fluid.

3. The method of claim 1 wherein the visual pattern comprises at least one ring, and wherein the step of comparing comprises comparing the area of the known volume of fluid to an area within the at least one ring.

4. The method of claim 1 wherein the visual pattern comprises a plurality of rings, and wherein the step of comparing comprises comparing the area of the known volume of fluid to an area of one ring of the plurality of rings.

5. The method of claim 4 wherein each ring of the plurality of rings signifies an acceptable level of cleanliness for different fluids.

* * * * *